United States Patent [19]

Imafuku et al.

[11] 4,271,001
[45] Jun. 2, 1981

[54] APPARATUS FOR MEASURING MEMBRANE CHARACTERISTICS OF VESICLES

[75] Inventors: Hiroshi Imafuku; Takeo Kimura; Hidehiko Kobayashi, all of Fuji, Japan

[73] Assignee: Asahi Kasei Kogyo Kabushiki Kaisha, Osaka, Japan

[21] Appl. No.: 20,688

[22] Filed: Mar. 15, 1979

[30] Foreign Application Priority Data

Mar. 23, 1978 [JP] Japan .................................. 53-32338
Mar. 5, 1979 [JP] Japan .................................. 54-25251

[51] Int. Cl.³ .......................................... G01N 27/42
[52] U.S. Cl. ............................... 204/195 B; 204/1 T; 204/195 R; 204/195 M
[58] Field of Search .......... 204/195 B, 195 R, 195 M, 204/1 T; 324/29

[56] References Cited

U.S. PATENT DOCUMENTS

| | | | |
|---|---|---|---|
| 3,421,982 | 1/1969 | Schultz et al. | 204/195 B X |
| 3,623,960 | 11/1971 | Williams | 204/1 T |
| 3,706,649 | 12/1972 | Cosgrove et al. | 204/195 M |
| 3,765,841 | 10/1973 | Paulson et al. | 204/195 R UX |
| 3,857,771 | 12/1974 | Sternberg | 204/195 B |
| 3,957,592 | 5/1976 | Young | 204/195 R X |
| 3,997,838 | 12/1976 | Shamos et al. | 204/195 R X |
| 4,003,705 | 1/1977 | Buzza et al. | 204/195 B X |

OTHER PUBLICATIONS

Makoto Muratsugu et al., Digests of Lectures, Second Symposium on Interaction Between Biomembranes and Drugs, (1978).
H. V. Malmstadt et al., J. Chemical Education, vol. 43, No. 7, pp. 340-353, Jul. 1966.

*Primary Examiner*—G. L. Kaplan
*Attorney, Agent, or Firm*—Sughrue, Rothwell, Mion, Zinn and Macpeak

[57] ABSTRACT

Vesicles are suspended in a lipophilic ion solution and the lipophilic ion concentration is changed by the permeation of the lipophilic ions into the vesicles. An electrode selectively responsive to the lipophilic ions is immersed in the suspension to detect the time-change rate of the electrode potential, thereby to obtain a change in the lipophilic ion concentration with respect to time, from which are measured membrane characteristics of the vesicles, such as the permeability of a vesicular membrane to the lipophilic ions.

7 Claims, 7 Drawing Figures

APPARATUS FOR MEASURING MEMBRANE CHARACTERISTICS OF VESICLES

BACKGROUND OF THE INVENTION

This invention relates to a method and an apparatus for measuring membrane characteristics of vesicles, such as the permeability coefficient to a lipophilic ion, the membrane potential, etc. by the employment of an electrode selectivity responsive to the lipophilic ion.

The vesicles mentioned in this invention are structural members which have a membrane permitting the permeation therethrough of a lipophilic ion enclosed with the membrane and a liquid capable of disolving the lipophilic ion, and including living cells, such as an animal cell, a plant cell, a bacterial cell, etc., organellas, such as mitochondria, chloroplast, etc. and artificially made vesicles such as liposome.

Recently many studies are being very actively done for the prescience of various diseases, identification of pathogenes, clarification of the effect of drugs on the biomembrane or screening of new bioactive substances by utilizing various functions of a biomembrane, especially, the transport capacity of the biomembrane.

Methods that have heretofore been employed for measuring the transport capacity of the biomembrane are such as follows: If a vesicle is put in a solution of a substance originally present in a living body, for example, glucose, the glucose flows in and out of the vesicle and, at the same time, water also flows in and out of the vesicle to increase and decrease its volume. By measuring the change in the light scattering intensity or turbidity of the cell suspension which accompanies the volume change of the vesicle, its permeability to the substance (glucose) is detected. In the case of erythrocytes, the permeability of the erythrocytic membrane of the substance is measured by detecting the time when water enters the erythrocytes to burst them to make the solution red, that is, how long it takes to cause hemolysis. Another method is to label the substance by isotope and measure the isotope having passed through the cell membrane, whereby to obtain the permeability of the cell membrane to the substance.

The radioisotope method is the most reliable but incapable of successive measurement and the radioactive material is harmful and should be handled very carefully; therefore, this method is not suitable for measurement of many samples. Since the method of measuring the volume change in the cell which results from the inflow and the outflow of water requires an inflow and an outflow of the substance in a large amount sufficient to deform the membrane, data obtained by this method do not often agree with the values measured by the radioisotope method. The substances used for conventional measurements of the permeability thereto of vesicles are almost those originally contained in the living cells to be measured or the circumstances in which the cells exist. Further, the conventional measurement of the permeability of the vesicular membrane is a mere measurement and the measured values are not utilized for prescience of diseases and like purposes.

An apparatus for measuring the membrane potential of a vesicle is set forth, for example, in "Membrane Potential Measurement Using Lipophilic Ions for Vesicles Directly Unmeasurable with Small Electrodes" by Makoto Muratsugu et al, Digests of Lectures, Second Symposium on Interaction between Biomembranes and Drugs, 1978. This apparatus employs an electrode selectively responsive to a lipophilic ion but is an apparatus for basic researches which is intended only to obtain membrane potentials of vesicles which have large membrane potentials, such as mitochondria, bacteria, etc. A method for measuring the membrane potential with this apparatus is to detect a potential difference $\Delta E$ between steady potentials of an electrode in a solution of lipophilic ions before and after the injection of vesicles into the solution and calculate the membrane potential of the vesicle by substituting into a complicated equation the potential difference value $\Delta E$, the volume value of the vesicle and the volume value of the solution suspending the vesicle. With this apparatus, since the steady potential of the electrode is measured after the injection of the vesicle into the solution, as mentioned above, the measurement must be retarded until the electrode potential becomes steady after the injection of vesicles. Generally, it takes time for the electrode potential to become steady after the injection of vesicles into the solution. Especially blood cells of human beings are small in both the membrane potential and the permeability coefficient; in particular, at low temperatures between 0° to 25° C., the permeating speed is low, so that it takes as long as more than 30 minutes for the electrode potential to become steady after the blood cells are injected into the solution. Such a conventional method of measurement requires a lot of time to measure the electrode potential difference $\Delta E$ and involves troublesome proceedings of calculating the membrane potential of the vesicle by substituting into a complicated equation the electrode potential difference $\Delta E$ measured for each sample, as described above. Therefore, it is impossible to measure the membrane potentials of a large number of samples in a clinical examination.

The permeability coefficient of the vesicular membrane to the lipophilic ion bears a close relation to the membrane fluidity of vesicles; the membrane potential is a difference between potentials on both sides of the vesicular membrane and a physical quantity which serves as a driving force for the ion transfer. The membrane potential and the membrane fluidity of vesicles are both dependent only upon the characteristics of the vesicular membrane and considered as basic factors which define the transport capacity of the vesicular membrane. If valuable information on the transfer of a substance through the vesicular membrane is obtained, it is possible to achieve, for example, the prescience of various diseases, identification of pathogenes, clarification of the effect of drugs on the biomembrane or screening of new bioactive substances.

SUMMARY OF THE INVENTION

A first object of this invention is to provide a method and an apparatus for directly and rapidly measuring basic factors which define the transport capacity of a vesicular membrane.

A second object of this invention is to provide a method and an apparatus for measuring the membrane characteristics of vesicles which enable the prescience of various diseases, identification of pathogenes or screening of new bioactive substances.

A third object of this invention is to provide a method and an apparatus for rapidly measuring the membrane potential which is one of the membrane characteristics of vesicles and/or the coefficient of permeability to lipophilic ions which is another membrane characteristic of the vesicles. In other words, this object is to provide a method and an apparatus which can be employed for measuring only the membrane potential of the vesicular membrane or only the permeability coefficient of the vesicular membrane for the lipophilic ions, or for simultaneously measuring both of them.

A fourth object of this invention is to provide a method and an apparatus which enable the membrane characteristics of vesicles at any time while lipophilic ions flow in and out of the vesicles.

A fifth object of this invention is to provide a vesicular membrane characteristic measuring method and apparatus which enables processing a large number of samples with one machine in a short time.

A sixth object of this invention is to provide a method and an apparatus which enables the membrane characteristics of vesicles of low membrane potential.

In accordance with this invention, by an electrode immersed in a liquid containing lipophilic ions and suspended vesicles and selectively responsive to the lipophilic ions, the rate of change of the lipophilic ion concentration with respect to time, based on the presence of the vesicles, is detected as the rate of change in the potential of the electrode with respect to time. That is, vesicles or their suspension is poured into a lipophilic ion solution or vice versa; in either case, the lipophilic ions flow in the vesicles to cause a change in the lipophilic ion concentration of the solution. This change is measured by the electrode which is selectively responsive to the lipophilic ions. The permeability characteristic of the vesicular membrane to the lipophilic ions and/or its membrane potential is obtained by an operation based on the rate of the detected potential change with respect to time, the volume of the lipophilic ion solution, the total volume and the total surface area of the vesicles suspended in the solution and a temperature. Alternatively, the rate of the detected potential change with respect to time is divided by the electrode potential difference change peculiar to the vesicles and the resulting value is used as an index of the permeability of the vesicular membrane for the lipophilic ions. During the measurement of the electrode potential, it is preferred to keep a vessel at a constant temperature.

DESCRIPTION OF THE PREFERRED EMBODIMENTS

Figure 1:
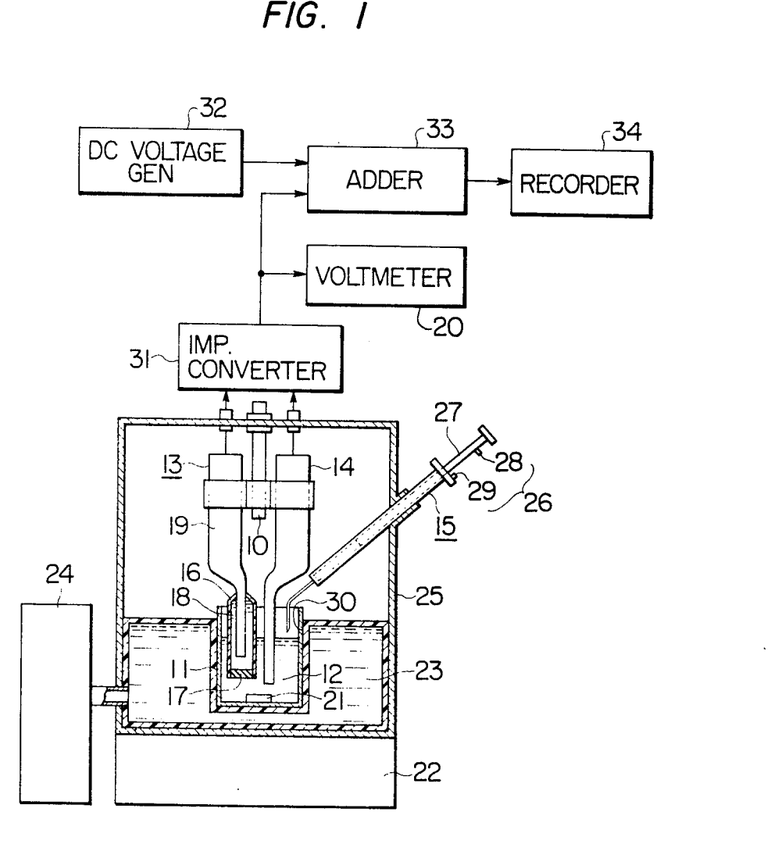
FIG. 1 is a schematic diagram showing an example of apparatus embodying the method of this invention.

Referring first to FIG. 1, reference numeral 11 indicates a vessel, which contains a solution 12 capable of dissolving lipophilic ions, vesicles being suspended in the solution 12. It is preferred that the vessel 11 is treated, for example, with silicone so as to prevent the vesicles from adhering to the inner wall of the vessel 11 and is made of a transparent material to permit easy observation from the outside. A lipophilic ion electrode 13 and a reference electrode 14 are partly inserted in the vessel 11 to make contact with the vesicle suspension therein. An injector 15 is provided for injecting vesicles into the vessel 11 in a certain volume. The injector 15 may be a syringe, a pippet or the like but it is preferred to use, for example, a micro syringe which is capable of injecting a constant volume of vesicles.

The solution 12 may be any kinds of solvents, so long as they uniformly dissolve a predetermined quantity of the lipophilic ions, but since the permeability coefficient and the membrane potential are greatly influenced by the property of the solution, it is preferred to employ a saline aqueous solution whose pH, ion composition, osmotic pressure are properly adjusted to fit the object of measurement. The lipophilic ions to be dissolved in the solvent solution may be either lipophilic cations or lipophilic anions and the ion concentration is preferred to be as low as possible in the range in which the response of the electrode 13 follows the Nernst's equation. The optimum vesicle concentration for suspending the vesicles can be selected as desired in accordance with the membrane potential of the vesicles and the SN ratio of the measuring apparatus used; but, in general, it is desirable that the volume of vesicles is in the range of 0.01 to 50% of the volume of the suspension 12. With less than 0.01%, the electrode potential variation is small to result in lowered measurement accuracy. Also in the case of more than 50%, the resulting permeability coefficient and the membrane potential are deviated from their true values because of an increase in the amount of adsorption of the lipophilic ions to the vesicular membrane. But the deviation is smaller than in the case of the conventional method, so that the volume of vesicles may in certain cases be selected outside of the abovesaid range.

The lipophilic ion may be positive or negative. As the lipophilic cation, use can be made of a quaternary cation which is expressed by a general equation, $R_4X^+$, where R is a hydrocarbon radical group or halogenated hydrocarbon group and X a nitrogen atom, phosphorus atom or arsenic atom. This R includes an alkyl group of methyl, ethyl, propyl, butyl, etc., an aryl group of phenyl, tolyl, etc., an aralkyl group of benzyl, etc., an cycloalkyl group of cyclohexyl, etc. and their halogen substitution products, such, for example, as chlorophenyl. As the quaternary cation indicated by the above general equation, use can be made of dibenzyldimethylammonium, benzylphenyldimethylammonium cation, tetraphenylphosphonium, tetraphenylarsonium and so on.

As the lipophilic anion, use can be made of an organoborate or a boron-carbanion cage compound which is expressed by a general equation, $R'_4B^-$, where $R'$ is a hydrocarbon radical group or halogenated hydrocarbon group. This R' includes an alkyl group of methyl, ethyl, propyl, butyl, etc., an aryl group of phenyl, tolyl, etc., an aralkyl group of benzyl, etc., an cycloalkyl group of cyclohexyl, etc. and their halogen substitution products, such, for example, as chlorophenyl. As the organoborate indicated by the above general equation, use can be made of tetraphenyl boron ion, tetratolyl boron ion, tetra (p-chlorophenyl) boron ion, etc. As the boron-carbanion cage compound, use can be made of dicarbaundecarborane, dicarbadodecaborane and dicarbaheptaborane substituted with a phenyl group, such as phenyldicarbaundecaborane and methyldicarbadodecahydroundecaborane.

The lipophilic ion electrode 13 is selectively responsive to the lipophilic ion present in the suspension 12 and may in some case be referred to as an organic ion electrode. Letting E and C represent the potential difference between the lipophilic ion electrode 13 and the reference electrode 14 and the lipophilic ion concentration of the suspension 12, respectively, any lipophilic ion electrode can be used, so long as it exhibits an electrode characteristic, such as given by the following equation (the Nernst's equation), in the range of the concentration C from $5 \times 10^{-6}$ to $1 \times 10^{-4}$ M:

$$E=(RT/ZF)ln(C/\alpha)$$

where $\alpha$ is a constant inherent to the electrode, T is the absolute temperature of the liquid in which the electrode is immersed, R is a gas constant, F is the Faraday constant and Z is the number of charges of the lipophilic ion. In the lipophilic ion electrode 13, a polymer film 17 having sealed therein, as a sensitive substance, an ion association of a lipophilic cation and a lipophilic anion is stuck to one end of a tube 16 made of, for example, glass or polymer. The tube 16 contains an aqueous solution having dissolved therein the desired lipophilic ion in a predetermined concentration, that is, the so-called reference solution 18. In the reference solution 18, one end of the reference electrode 19, such as a commercially available silver-silver chloride electrode is sealed. The electrode 13 is immersed in the suspension 12 on the side of the polymer film 17. The reference electrode 14 may be a silver-silver chloride electrode placed on the market.

It is preferred to design the apparatus so that the vesicles in the solution 12 do not settle during measurement. For example, a stirring rotor 21 formed with a magnet is disposed in the solution 12 in the vessel 11 and an electromagnetic stirrer 22, which is controlled to rotate at a constant speed, is provided under the vessel 11. By the magnetic attractive force between the electromagnetic stirrer 22 and the rotor 21, the latter is rotated at a constant speed to prevent settlement of the vesicles in the solution 12. In this case, in order to lessen the danger of the vesicles being impaired by the rotor 21, it is desirable to minimize the rotating speed of the rotor 21 in the range in which the vesicles do not settle. Further, since the rotating speed of the rotor 21 has an affect on the potential of the electrode 13, it is preferred to drive the rotor 21 at a constant speed.

As the potential of the electrode 13 varies sharply in response to a change in the measurement temperature, it is preferred to dispose the vessel 11, for example, in a constant-temperature bath 23. In FIG. 1, the vessel 11 is shown to be housed in a hollow 30 formed at the center of the constant-temperature bath 23. The warm water in the constant-temperature bath 23 is circulated by a pump 24 to be held at a constant temperature. For high measurement accuracy, it is desirable that measurement is conducted with a temperature variation of $\pm 0.1°$ C. In the case where there is a fear that noises by electrostatic induction or some other electromagnetic noises get mixed in the measurement system, the vessel 11 and the electrodes 13 and 14 are disposed in a shield box 25. Other elements which do not generate electromagnetic noises may be housed in the shield box 25, as required. The shield box 25 may be made of any materials which cut off electromagnetic waves. But in the case of agitating the vesicle suspension 12 by means of the electromagnetic stirrer 22, it is rather preferred to place the electromagnetic stirrer 22 on the outside of the shield box 25 so as to cut off noises from the electromagnetic stirrer 22. In such an instance, the wall portion of the shield box 25 contactng the electromagnetic stirrer 22 is made of a material permitting the passage therethrough of lines of magnetic force, for example, aluminum or stainless steel, so as to drive the rotor 21 in the vessel 11. A mounting rod 10 is fixed to the inside of the top panel of the shield box 25 and the electrodes 13 and 14 are supported by the rod 10.

In order that the output potential of the lipophilic ion electrode 13 is applied, as an electric signal with respect to time, to an arithmetic unit, there is provided in the injector 15 a trigger signal generator 26 which generates a trigger signal for designating the time of starting the application of the abovesaid output potential. For example, upon completion of injection of a sample containing vesicles, a projection 28 mounted on an operating rod 27 of the injector 15 drives a micro switch 26 disposed on the case of the injector 15 to produce a trigger signal. The trigger signal generation may occur at the start of injection of vesicles or during the injection; in short, the trigger signal generation suffices only to inform the arithmetic unit of the injection of vesicles into the solution 12.

A voltage signal indicating the potential difference between the lipophilic ion electrode 13 and the reference electrode 14 is supplied to an impedance converter 31, as needed, and the voltage signal available between the electrodes 13 and 14 is converted to a signal output of low impedance. Further, it is desirable to provide a voltmeter 20 for reading the potential difference between the electrodes 13 and 14; it is advantageous to refer to the potential difference throughout the subsequent operations. From this point of view, it is preferred that the gain of the impedance converter 31 is 1. In the present invention, since very small potential variations are measured, it is desirable that the zero point potential has little drift and that the impedance converter 31 is of few noises.

In this apparatus, a quantity desired to obtained is derived from a small change in the potential difference between the electrodes 13 and 14, so that the measurement accuracy is enhanced if only the change of the potential difference is enlarged. To this end, a suitable DC voltage opposite in sign to the output signal from the impedance converter 31 is obtained from a small DC voltage generator 32 in accordance with the detected potential difference between the electrode pair and is applied to an adder 33 together with the output signal from the impedance converter 31 for the purpose of cancelling a certain voltage in the output signal from the impedance converter 31. The output signal of the adder 33, from which a certain voltage has been removed as required, is supplied to a recorder 34.

In the measurement, vesicles are put first in the suspension 12 without lipophilic ions and after the potential difference between the electrodes 13 and 14 has reached a constant value, the lipophilic ions are added to the suspension 12, thereby to change the concentration of the lipophilic ions in the vesicle suspension. Alternatively, after the potential difference between the electrodes 13 and 14 immersed in the suspension 12 containing both the vesicles and the lipophilic ions has become constant, a liquid of a lipophilic ion concentration different from that of the abovesaid suspension is added to the suspension to alter the lipophilic ion concentration of the vesicle suspension. The rate of change in the potential difference between the electrodes 13 and 14 with respect to time is measured after the lipophilic ion concentration has abruptly been changed, as described above. But, if the lipophilic ion electrode 13 is immersed in the suspension containing no lipophilic ions, there is the possibility that the lipophilic ions sealed in the polymer film 17 go out into the solution to cause a change in the electrode potential. To avoid this, it is preferred to measure the rate of variations in the potential difference between the electrodes 13 and 14 with respect to time which accompany a change in the lipophilic ion concentration of the lipophilic ion solution 12 which is caused by adding thereto vesicles or a vesicle suspension.

In the measurement by the apparatus shown in FIG. 1, it is preferred to agitate the lipophilic ion solution 12 at a constant speed to such a degree as not to impair the activity of vesicle, while maintaining the solution 12 at a proper, desired temperature in the range from 0° to 100° C. which is presumed from the living environment of the vesicles to be measured, and to perform the subsequent operation after making sure that the potentials of the electrodes 13 and 14 have become constant. That is, the vesicle or a vesicle suspension is injected by the injector 15 into the liquid 12. The changes in the electrode potentials caused by this injection are recorded. The potential changing rate immediately after the injection of the vesicle suspension is made an index of the permeability of the vesicular membrane for the lipophilic ions. Preferably, the ratio of the potential changing rate immediately after the injection of vesicle to the amount of potential changes until the potential becomes constant again after the injection of vesicles is used as the index of the lipophilic ion permeability of the vesicular membrane. For the calculation of this index, the recorded results of the recorder 34 are read out, or use can also be made of an arithmetic unit described later. The difference between the potential before suspending the vesicle and the potential restored to its constant value after the injection of the vesicle is defined as an electrode potential difference change, which is inherent to each particular vesicle. Accordingly, in the case of measuring many samples of the same kind of vesicle, the electrode potential difference change once measured can be used as the index of the permeability for the other measurements.

Figure 2:
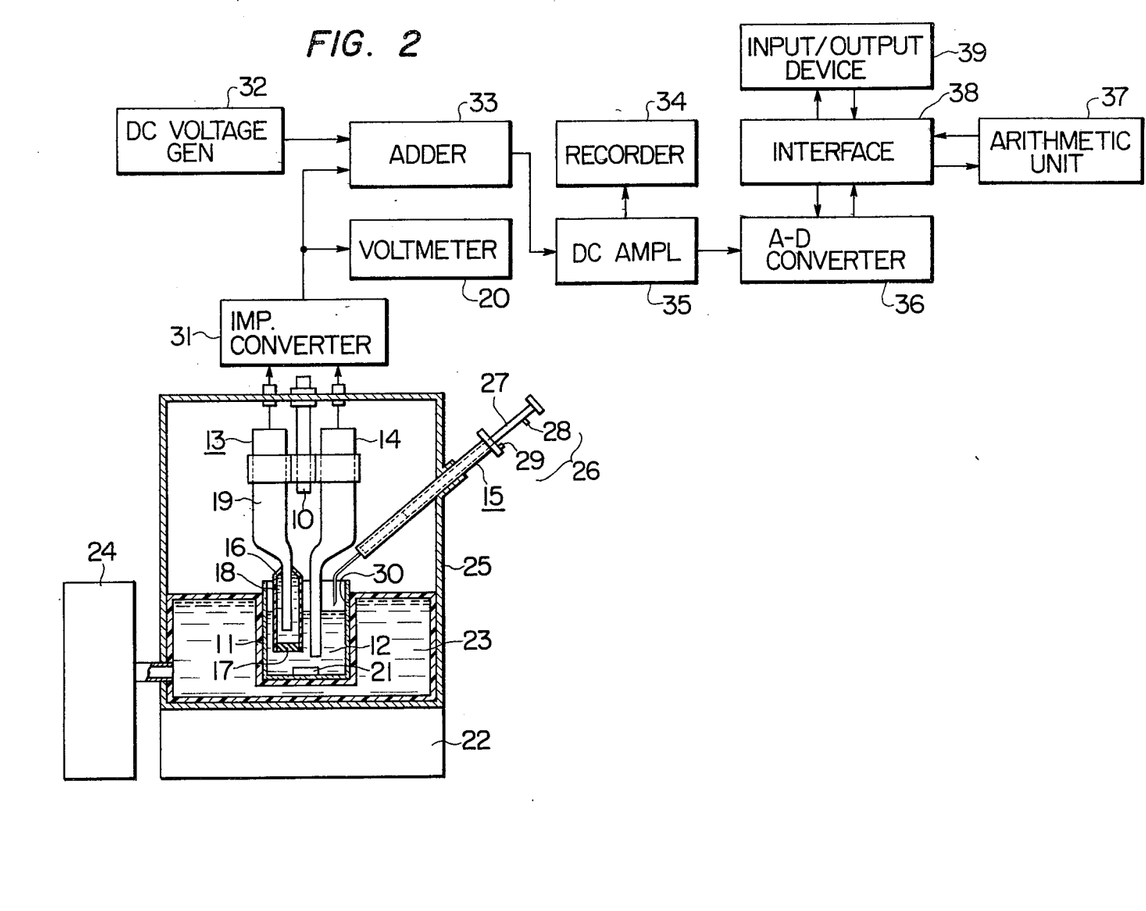
FIG. 2 is a schematic diagram illustrating another example of this invention in which an arithmetic unit is added to the apparatus of FIG. 1.

FIG. 2 shows another example of this invention in which the membrane characteristic of vesicle is calculated by an arithmetic unit from the detected electrode potential variations. In FIG. 2, parts corresponding to those in FIG. 1 are identified by the same reference numerals. The output from an adder 33 is amplified by a DC amplifier 35, as required, and the amplified output is recorded by the recorder 34 and, at the same time, applied to an A-D converter 36. The DC amplifier 35 may be any type of DC amplifier, so long as it has such a gain as to provide an output signal suitable for input to the A-D converter 36, and are of little drift and noise. The recording with the recorder 34, permits easy recognition of whether the noise and drift of the detected potential difference between the electrodes 13 and 14 has been reduced or not, that is, whether the noise and drift lies within the predetermined limits or not. It is also possible to employ an analog arithmetic unit as the arithmetic unit 37 and apply the detected electrode potential signal as an analog signal to the arithmetic unit without converting the detected signal to digital form, but when high measurement accuracy is required, a digital arithmetic unit is used. In this instance, the analog signal from the DC amplifier 35 is converted by the A-D converter 36 to digital form for input to the arithmetic unit 37 via an input/output control interface 38. It is desirable that the resolution of the A-D converter 36 is more than 8 bits. The output from the A-D converter 36 is applied to the arithmetic unit 37 at regular time intervals or at such programmed intervals such that the converter output is provided first at short time intervals and then at gradually longer time intervals. The output from the A-D converter 36 is stored in a memory of the arithmetic unit 37.

Where high measurement accuracy is not needed, the arithmetic unit 37 may be an analog one, as mentioned above, and it is also possible to use an analog and a digital arithmetic unit in combination. In the case of the digital arithmetic unit, an ordinary microcomputer can be employed. In the case of measuring the membrane potential of vesicle and/or the permeability coefficient of the vesicular membrane to the lipophilic ion by the arithmetic unit 37, data necessary for the arithmetic operation, that is, data except the electric signal with respect to time and the detected potential outputs from the electrodes, for example, the volume of the liquid 12 having suspended therein the vesicle, the total volume and the total surface area of the vesicle suspended in the liquid 12 and/or the temperature of the liquid 12, are inputted via an input/output device 39 to the arithmetic unit 37.

When a sample containing vesicle is injected from the injector 15 to the vessel 11, the detected electrode potentials may in certain cases abruptly change due to the effect that the lipophilic ion concentration in the solution 12 is diluted by the liquid contained in the sample, and some other effects. For example, in the case of measuring the membrane characteristic of erythrocytes, when blood is injected into the vessel 11, the electrode potentials abruptly decrease for first 10 to 20 seconds and then gradually decrease owing to incorporation of the lipophilic ion in the liquid into the erythrocytes. Accordingly, for the purpose of preventing the influence of such initial variations of the electrode potentials by the vesicle injection, it is preferred to start the arithmetic operation after the change in the potential difference between the electrodes 13 and 14 is caused only by the permeation of the lipophilic ion into the vesicle after suspending the vesicle into the liquid 12 and stop the arithmetic operation at a proper time after confirming that the permeability coefficient and/or the membrane potential are respectively converged to certain values. For determining the moment of starting the arithmetic operation, the trigger signal from the trigger signal generator 26 is provided via the input/output interface 38 to the arithmetic unit 37.

The data outputted via the data input/output device 39 are the permeability coefficient of the vesicular membrane to the lipophilic ion and/or the membrane potential of the vesicle, but it is also possible to output one part of the data inputted into the arithmetic unit 37 and a parameter representing the adaptability of the measured value to theory. The data outputting is achieved by printing with a printer or a display with a CRT display. Moreover, the volume of the liquid 12 having suspended therein the vesicle, the total volume and the total surface area of the vesicle injected into the liquid and/or the temperature of the vessel 11 are entered by a keyboard input device and set in a memory of the arithmetic unit 37. Also, it is possible to set the various data by the so-called digital switches and read them out of the arithmetic unit 37 as required, or to set one part of the data by keyboards and the other part by digital switches.

Next, a description will be given of an example of the arithmetic operation which is conducted by the arithmetic unit 37 in the case of high-accuracy measurement. In this example, the permeability coefficient P of the vesicular membrane to the lipophilic ion and the membrane potential $\Psi m$ of the vesicle are calculated on the basis of the following equations:

$$P = \frac{(1+\xi)e^{\hat{a}} + (1+\xi-\eta)\hat{b}}{\xi\eta\zeta \ln\frac{(\eta-1)\hat{b} - e^{\hat{a}}}{\xi(\hat{b} + e^{\hat{a}})}} \quad (1)$$

$$\Psi m = -\frac{RT}{ZF} \ln \frac{(\eta-1)\hat{b} - e^{\hat{a}}}{\xi(\hat{b} + e^{\hat{a}})} \quad (2)$$

wherein R is a gas constant, F is the Faraday constant, Z is the number of charges of the lipophilic ion, T is the absolute temperature of the liquid 12 having suspended therein the vesicle, e is the base of a natural logarithm, ln is an operand of the natural logarithm and $\xi$, $\eta$ and $\zeta$ are the quantities defined by the following equations:

$$\xi \equiv V^{II}/V^{I} \quad (3)$$

$$\eta \equiv \exp[(ZF/RT)(E(O) - E(t_0))] \quad (4)$$

$$\zeta \equiv A/V^{II} \quad (5)$$

wherein $V^I$ is the volume of only the liquid 12 that the total volume of the vesicle, i.e. the sum of the volumes of the vesicles, $V^{II}$ is subtracted from the total volume of the vesicle suspension, A is the total surface area of the vesicle, i.e. the sum of the surface area of the vesicles, E(O) is the electrode potential corresponding to the lipophilic ion concentration in the liquid 12 immediately after the vesicles are suspended therein but before the lipophilic ions are not as yet incorporated into the vesicles, and $E(t_0)$ is the electrode potential at a moment $t_0$ of starting the arithmetic operation which can be determined at will.

$\hat{a}$ and $\hat{b}$ are most probable values of coefficients a and b based on the assumption that y(t) defined by the following equation (6) is represented by a straight line expressed by the following equation (7).

$$y(t) = \ln\left\{-\frac{ZF}{RT} \exp\left[\frac{ZF}{RT}(E(t) - E(t_0))\right] \frac{d}{dt} E(t)\right\} \quad (6)$$

$$y(t) = a + b(t - t_0) \quad (7)$$

These $\hat{a}$ and $\hat{b}$ can be determined, for example, by the method of least squares. Since y(t) is calculated from the electrode potential E(t) at an arbitrary moment t in accordance with the equation (6), if the values of y(t) at moments $t_0, t_1, t_2, \ldots t_n$ when the output from the A-D converter 36 is applied to the arithmetic unit 37 are respectively represented by $y_0, y_1, y_2, \ldots y_n$, $\hat{a}$ and $\hat{b}$ are calculated by the following equations:

$$\hat{b} = \frac{\sum_{i=0}^{n}(t_i - t_0 - \bar{\tau})(y_i - \bar{y})}{\sum_{i=0}^{n}(t_i - t_0 - \bar{\tau})^2} \quad (8)$$

$$\hat{a} = \bar{y} - \hat{b}\bar{\tau} \quad (9)$$

where $$\bar{\tau} = \frac{1}{n+1} \sum_{i=0}^{n}(t_i - t_0) \quad (10)$$

$$\bar{y} = \frac{1}{n+1} \sum_{i=0}^{n} y_i \quad (11)$$

Next, a description will be made of the process in which the equations (1) and (2) were derived. The flux $\phi(t)$ of the lipophilic ions flowing across the vesicular membrane when the lipophilic ion concentration in the vesicle having the potential $\Psi m$ on the inside of the vesicular membrane at a given moment t is $C^{II}(t)$ and the lipophilic ion concentration in the liquid 12 at the moment t is $C^{I}(t)$, is given by the following equation:

$$\phi(t) = -\frac{PZF\Psi m}{RT} \cdot \frac{C^{I}(t) - C^{II}(t)\exp(ZF\Psi m/RT)}{1 - \exp(ZF\Psi m/RT)} \quad (12)$$

For the derivation of the equation (12), refer to such a literature as, for example, J. R. Sacks et al; Transport through Red Cell Membranes, In "The Red Blood Cell" edited by D. M. Surgenor, Second Edition, Vol. 2, p613–p703, Academic Press, 1975. What is measured by the apparatus of FIG. 2 is the lipophilic ion concentration $C^{I}(t)$ in the liquid 12, and the following relationship exists between the concentration $C^{I}(t)$ and the flux $\phi(t)$:

$$\frac{d}{dt} C^{I}(t) = -\frac{\phi(t)A}{V^I} \quad (13)$$

and the following relationship is established between the concentrations $C^{I}(t)$ and $C^{II}(t)$:

$$C^{I}(t)V^{I} + C^{II}(t)V^{II} = \text{constant} = C^{I}(O)V^{I} \quad (14)$$

where $C^{I}(O)$ is the lipophilic ion concentration in the liquid 12 before suspending therein the vesicles. In the following analysis, it is assumed that the moment when the vesicles are suspended in the liquid 12 is the moment O. Eliminating the flux $\phi$ and the concentration $C^{II}(t)$ from the equations (12), (13) and (14), it follows that $$\frac{dC^I}{\{V^I + V^{II}\exp(-ZF\Psi m/RT)\}C^I - C^I(O)V^I} = \frac{PZF\Psi mAdt}{RTV^IV^{II}\{\exp(-ZF\Psi m/RT) - 1\}} \quad (15)$$

Changing the equation (15) by integrating from the moment $t_0$ to t, the following equation is obtained:

$$\frac{\left\{1 + \frac{V^{II}}{V^I} \exp(-ZF\Psi m/RT)\right\} C^I(t) - C^I(0)}{\left\{1 + \frac{V^{II}}{V^I} \exp(-ZF\Psi m/RT)\right\} C^I(t_0) - C^I(0)} = \quad (16)$$

$$P \frac{ZF\Psi m}{RT} \frac{A}{V^{II}} \times \frac{1 + \frac{V^{II}}{V^I} \exp(-ZF\Psi m/RT)}{\exp(-ZF\Psi m/RT) - 1} (t - t_0)$$

Introducing the following parameter $$\exp(-ZF\Psi m/RT) \equiv X \quad (17)$$

and substituting the equations (3), (5) and (17) into the equation (16), the following equation is obtained:

$$\frac{(1 + \xi X)C^I(t) - C^I(0)}{(1 + \xi X)C^I(t_0) - C^I(0)} = X(-P\zeta \frac{1 + \xi X}{X - 1})(t - t_0) \quad (18)$$

It has been ascertained by actual measurement that the potential E of the lipophilic ion electrode 13 immersed in the lipophilic solution 12 having the concentration C is given by $$E = (RT/ZF)ln(C/\alpha) \quad (19)$$

in the concentration range in which the concentration C is between $5 \times 10^{-6}$ M and $1 \times 10^{-2}$ M. $\alpha$ is a constant inherent to the electrode 13. Letting E(O), E(t$_0$) and E(t) respectively represent the electrode potentials corresponding to the lipophilic ion concentrations $C^I(O)$, $C^I(t_0)$ and $C^I(t)$ in the vesicle suspension 12 at the moments O, $t_0$ and t, the equation (18) becomes as follows:

$$\frac{(1 + \xi X) \cdot \exp(ZFE(t)/RT) - \exp(ZFE(0)/RT)}{(1 + \xi X) \cdot \exp(ZFE(t_0)/RT) - \exp(ZFE(0)/RT)} = \quad (20)$$

$$X(-P\zeta \frac{1 + \xi X}{X - 1})(t - t_0)$$

Changing the equation by differentiating its both sides with respect to time and substituting the equation (4) into the equation (20), the following equation is resulted:

$$\ln[-\frac{ZF}{RT} \frac{dE(t)}{dt} \exp[\frac{ZF}{RT}\{E(t) - E(t_0)\}] = \quad (21)$$

$$\ln[\frac{P\zeta \ln X}{X - 1}(\xi X + 1 - \eta)] - (P\zeta \frac{1 + \xi X}{X - 1} \ln X)(t - t_0)$$

The left side of the equation (21) is in agreement with y(t) of the equation (6). Further, letting the respective terms of the right side of the equation (21) to be as follows:

$$a \equiv \ln[\frac{P\zeta \ln X}{X - 1}(\xi X + 1 - \eta)] \quad (22)$$

$$b \equiv -P\zeta \frac{1 + \xi X}{X - 1} \ln X \quad (23)$$

the equation (21) can be regarded as a linear equation, such as the equation (7). The left side, y(t), of the equation (7) is a quantity which is calculated from the electrode potential E(t) at the given moment t in accordance with the equation (6), so that if the method of least squares is applied to the equation (7), the most probable values â and b̂ of the coefficients a and b can be obtained with the equations (8) and (9). Moreover, if the equations (22) and (23) are allied together and solved in connection with P and X and if use is made of the relation of the equation (17), P and $\Psi m$ can be obtained as functions of a and b, so that if the most probable values â and b̂, obtained as mentioned above, are substitued into them, the permeability coefficient and the membrane potential are obtained as the most probable values, as expressed by the equations (1) and (2).

E(0) is, as already defined, the electrode potential corresponding to the lipophilic ion concentration in the liquid 12 in the state that the lipophilic ions do not as yet become incorporated into the vesicles immediately after the vesicles are suspended in the liquid 12. To accurately obtain this potential E(0), the following correction is made for the electrode potential before the vesicles are suspended in the liquid 12. It is the correction for the electrode potential variation which is caused by the effect of dilution of the lipophilic ion concentration in the vesicle suspension 12 by the liquid contained in the sample injected from the injector 15 and the effect of adsorption of the lipophilic ions to the vesicular membrane. To make such a correction, the adsorption effect is estimated by using a sample which is identical with that contained in the injector 15 and in which all the vesicles contained are burst, and the dilution effect is estimated by measuring the amount of liquid contained in the sample. But when not so high accuracy is required, the purpose can sufficiently be attained even by using, as E(0), the electrode potential at the moment when the electrode potential begins to change owing only to the permeation of the lipophilic ions into the vesicles.

The aforesaid example of arithmetic operation is developed from the equation (12). It is also considered that as a result of further studies of transport phenomena of biomembranes, an equation representing the flux, further developed from the equation (12), may be derived in recognition to the structural difference among vesicles, but it is needless to say that also in such a case, the purpose can be accomplished by properly changing the aforesaid arithmetic operation.

Figure 3:
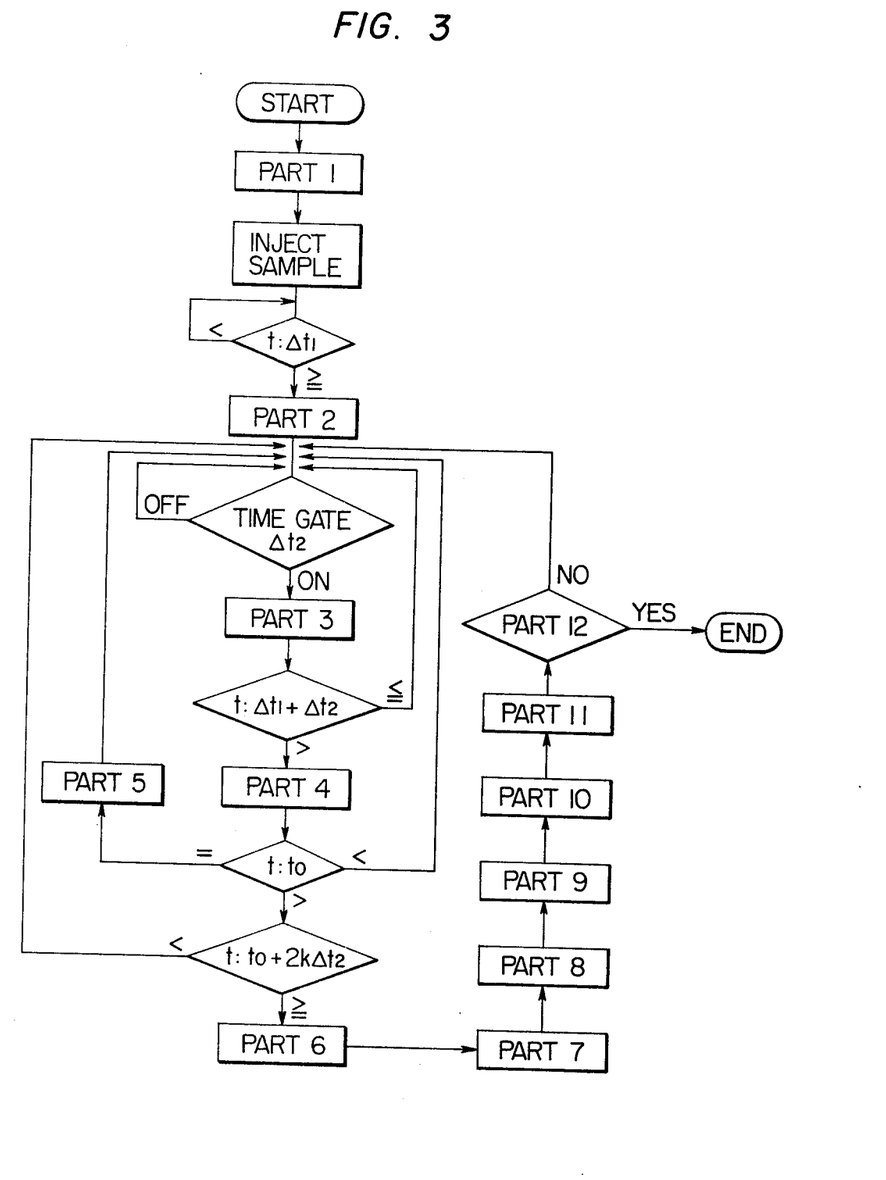
FIG. 3 is a flow chart showing an example of an arithmetic program of an arithmetic unit 37.

Turning next to FIG. 3, a brief description will be given in respect of an example of a program for actually calculating the permeability coefficient P of the vesicular membrane for the lipophilic ion and/or the membrane potential $\Psi m$ of the vesicle. The program is roughly divided into the following twelve parts. In the part 1 in FIG. 3, data necessary for the arithmetic operation are read out of the input/output device 39 and $\xi$ and $\zeta$ are calculated by the equations (3) and (4) and data to be recorded are recorded via the input/output device 39. The data to be inputted are the number of charges Z of the lipophilic ion, the absolute temperature T of the liquid 12 for suspending vesicles, the volume $V^I$ of only the liquid 12, the total volume $V^{II}$ and the total surface area A of the vesicles in a sample, a quantity determined by measurement conditions such as a cancel voltage generated by the small voltage generator 32 and so on, and artificial parameters necessary for executing the programs of part 2 et seq, for example, a time interval $\Delta t_1$ from the injection of the sample to the start of inputting of the output from the A-D converter 36 to the arithmetic unit 37, and if the subsequent input is achieved at regular time intervals, the time interval $\Delta t_2$ and the moment $t_0$ of the start of the arithmetic operation. But those of the above data which may be fixedly employed, for example, the number of charges Z of the lipophilic ion and the artificial parameters are rather preferred to be prestored in the arithmetic unit 37 together with the gas constant R and the Faraday constant F. Further, in connection with those of the above data whose values may be calculated from measured values easily obtainable by other means, for example, the total volume $V^{II}$ and the total surface area A of the vesicles in the sample to be injected, it is preferred to program the processes of their arithmetic operations and incorporated them in the part 1 and to obtain the values of desired data by directly inputting measured values, for instance, the volume of the sample to be injected, the ratio of the volume of the vesicles to that of the sample and the number of vesicles in the sample. The data which are desirable to be recorded are the measurement conditions, such as the temperature of the liquid for suspending therein the vesicles and so on, and the aforesaid artificial parameters.

A sample is injected by the injector 15 into the vessel 11 and, at the same time, a timer in the arithmetic unit 37 is started and at a moment after a proper time interval $\Delta t_1$ designated by the input data of the part 1, the output from the A-D converter 36 is applied as VAL(0) to the arithmetic unit 37 in the part 2. 0 is always stored in the leading array element ARG(0) of an array for storing the values of the respective moments.

After the lapse of the time interval $\Delta t_2$ designated in the procedure inputted in the part 1, the output from the A-D converter 36 is taken in the arithmetic unit 37 and then after the lapse of $\Delta t_2$, the output from the A-D converter 36 is again applied to the arithmetic unit 37. These values are sequentially stored as VAL(1) and VAL(2) in a memory of the arithmetic unit 37 and, at the same time, the moments of their storage are stored as ARG(1) and ARG(2). Upon storing of VAL(2), the operation proceeds to the part 4 and a differential coefficient is obtained by the forward difference method in accordance with the following equation:

$$DER(i) = \frac{VAL(i+1) - VAL(i)}{ARG(i+1) - ARG(i)}$$

where $i = 0, 1, 2, \ldots$ The resulting value is stored as DER(i) in a memory. Until the arithmetic operation starting moment $t_0$ designated in the part 1 is reached, it is repeated that the output from the A-D converter 36 is stored to store its value VAL(i) and the moment ARG(i) in the part 3 at the time interval $\Delta t_2$ and that the differential coefficient is obtained in the part 4.

When the arithmetic operation starting moment $t_0$ designated in the part 1 has thus been reached, the output from the A-D converter at that time is stored as $E(t_0)$ in the part 5, and $\eta$ is calculated in accordance with the equation (4). After the lapse of time $\Delta t_2$, the output from the A-D converter 36 is stored in the part 3 and the arithmetic operation for the differential coefficient is performed in the part 5. Until a time $k\Delta t_2$ (k being an integer larger than unity) has passed after the moment $t_0$, the parts 3 and 4 are repeated, and after the lapse of time $2k\Delta t_2$, the differential coefficients obtained in the period $2k\Delta t_2$ are averaged in the part 6. The number of differential coefficients to be added together for calculating the average value is $2k+1$, k being prestored in the arithmetic unit 37 or inputted in the part 1. It is at a moment $t_0 + k\Delta t_2$ that the value of differential coefficient thus averaged in consideration of the values of preceding and following differential coefficients, that is, the shifting averaged value of differential coefficient is assigned, and this value of differential coefficient is stored as AVDER(i). That is, when $i_0$ is assumed to be a minimum integer larger than $(t_0 - \Delta t_1)/\Delta t_2$, the average value is as follows:

$$AVDER(i) = \frac{1}{2k+1} \sum_{j=i-k}^{i+k} DER(j)$$

$$i = i_0 + 1, i_0 + 2, \ldots$$

with respect to the value i larger than $i_0$. In this manner, the average value of differential coefficient is obtained at the time interval $\Delta t_2$.

In the part 7, the left side, y(t), of the linear equation (7) are calculated from the stored VAL(i) and the calculated AVDER(i) in accordance with the equation (6) and the calculation result is stored as Y(I). That is, $$Y(i) = \frac{ZF}{RT}(VAL(i) - VAL(t_0)) +$$

$$\ln[-\frac{ZF}{RT} \cdot AVDER(i)]$$

where $i = i_0 + 1, i_0 + 2, \ldots$ Preparations are made for applying the method of least squares in the part 8. That is, $$DATAX(i) = ARG(i_0 + i) - ARG(i_0 + 1)$$

$$DATAY(i) = Y(i_0 + i)$$

where $i = 1, 2, \ldots$

In the part 9, most probable values $\hat{a}(i)$ and $\hat{b}(i)$ of until then are obtained by the method of least squares, with the linear equation, $y(t) = a + b(t - t_0)$, applied to the function y(t). That is, $\hat{a}(i)$ and $\hat{b}(i)$ are obtained pursuant to the equations (8) and (9) and its program is, in FORTRAN, as follows:

DIMENSION DATAX(300), DATAY(300)
SUMX=0
SUMY=0
N=0
SUMXX=0
SUMXY=0
The above program is placed at the beginning of the entire program, and the subsequent program is executed upon each storing of new data in DATAX(i) and DATAY(i).
SUMX=SUMX+DATAX(I)
SUMY=SUMY+DATAY(I)
N=N+1
AN=N
XM=SUMX/AN
YM=SUMY/AN
SUMXX=SUMXX+DATAX(I)**2
SUMXY=SUMXY+DATAX(I)*(DATAY(I)−YM)
B=(SUMXY−SUMX*SUMY/AN)/(SUMXX−SUMX**2/AN)
A=YM−B*XM
With the above program, the most probable values $\hat{a}(i)$ and $\hat{b}(i)$ of the coefficient to that moment are obtained.

To check the adaptability of the measured value to theory in part 10, the correlation coefficient between the measured value of y(t), i.e. DATAY(i) and the estimated value $$YHAT(i) = \hat{a} + \hat{b} * DATAX(i)$$

of y(t) is obtained. This program, stated in FORTRAN, is as follows:

```
DIMENSION YHAT(300)
SUMZ=0
SUMYY=0
SUMYZ=0
SUMZZ=0
```

The above program is placed at the beginning of the entire program and the following program is executed upon each storage of new data in DATAX(i) and DATAY(i).

```
SUMZ=SUMZ+YHAT(I)
ZM=SUMZ/AN
SUMYY=SUMYY+DATAY(I)**2
SUMYZ=SUMYZ+DATAY(I)*(YHAT(I)−ZM)
SUMZZ=SUMZZ+YHAT(I)**2
RYYHAT=(SUMYZ−SUMY*SUMZ/AN)/(-
   (SUMYY−SUMY**2/AN)*(SUMZZ−SUMZ**-
   2/AN))**0.5
```

With the above, the correlation coefficient RYYHAT(i) between the measured valued and the estimated value of y(t) to that moment is obtained.

In the part 11, most probable values P(i) and $\Psi m(i)$ of the permeability coefficient and the membrane potential to that moment are obtained. That is, P(i) and $\Psi m(i)$ are obtained by substituting into the equations (1) and (2) the values of $\xi$ and $\zeta$ obtained in the part 1, $\eta$ obtained in the part 5 and $\hat{a}(i)$ and $\hat{b}(i)$ obtained in the part 9.

In the part 12, if the following relationships are established among the values of P(i) and $\Psi m(i)$ obtained in the part 11, the values of P(i−1) and $\Psi m(i−1)$ similarly obtained by the immediately preceding operation in the part 11 and predetermined parameters $\epsilon_1$ and $\epsilon_2$, the resulting RYYHAT(i), P(i) and $\Psi m(i)$ are recorded via the data input/output device 39 and the arithmetic operation is stopped.

$$\left| \frac{P(i) - P(i-1)}{P(i)} \right| < \epsilon_1$$

$$\left| \frac{\Psi m(i) - \Psi m(i-1)}{\Psi m(i)} \right| < \epsilon_2$$

$\epsilon_1$ and $\epsilon_2$ are predetermined parameters which define the converged states, and are usually preferred to have values in the range of 0.005 to 0.1. Where the required accuracy is 1%, $\epsilon_1$ and $\epsilon_2$ are selected to be 0.01. When the calculated P(i) and $\Psi m(i)$ are not converged, the storing of the output from the A-D converter 36 at the time interval $\Delta t_2$, the calculation of the differential coefficient, the averaging of the differential coefficient and the other arithmetic operations for P(i) and $\Psi m(i)$, described above, take place.

The program described above is an example of obtaining the permeability coefficient and the membrane potential on the basis of the equations (1) and (2) and, needless to say, is not limited specifically thereto. For example, the time interval in which the output from the A-D converter 36 is applied to the arithmetic unit 37 need not always constant and may also be a properly programmed one. Further, the program mentioned above employs as E(0) in the equation (4), the electrode potential at the moment when the electrode potential starts to change as a result of the permeation of the lipophilic ions into the vesicles. But if the program is so adapted to use, as E(0), the potential obtained by making corrections for the dilution effect and the adsorption effect in connection with the electrode potential before the suspending of vesicles, there is no need of starting the inputting of the electrode potential to the arithmetic unit 37 immediately after the injection of vesicle as in the abovesaid program; and it is possible to perform the arithmetic operation at any desired time until the electrode potential is restored to its steady state, thereby to achieve the object.

Next, a description will be made with regard to the procedure for practising the method of this invention by the use of the apparatus of this invention shown in FIG. 2. At first, a power source switch (not shown) of the apparatus of FIG. 2 is turned on to sufficiently warm it up. Especially the electrode potential is sensitive to temperature, so that it is made sure whether or not the temperature of the constant-temperature bath 23 is controlled within a permissible temperature range. A certain volume of aliquot is withdrawn from a liquid which meets the conditions required corresponding to vesicles to be suspended and which has dissolved therein lipophilic ions in as low a concentration as possible within a range in which the response of the electrode to the lipophilic ions follows the Nernst's equation, and the aliquot is put in the vessel 11. The electrode 13 selectively responsive to the lipophilic ions and the reference electrode 14 are immersed in the liquid 12 and the potential difference between the both electrodes 13 and 14 is read out on the meter 20 connected to the output side of the impedance converter 31. A voltage which is substantially equal in magnitude to the read-out voltage and opposite in sign thereto is produced by the small DC voltage generator 32, and this voltage is added by the adder 33 to the output from the impedance converter 31 to obtain a signal whose voltage has been cancelled by a certain value. This signal is amplified by the DC amplifier 35 and applied to the recorder 34. It is desirable to provide a proper noise filter on the output side of the amplifier 35 so as to reduce noises in the output from the DC amplifier 35. After it is made sure by the record of the recorder 34 that the drift of the output from the amplifier 45 has been reduced to lie within a predetermined range, the data necessary for the aforesaid arithmetic operation, except the output from the A-D converter 36, are inputted via the data input/output device 39 to the arithmetic unit 37.

After completion of inputting of the data, a certain volume of vesicles adjusted for each particular purpose is injected by the injector 15 into the vessel 11. When a proper period of time prestored in the arithmetic unit 37 has passed after completion of the injection, the output from the A-D converter 36 is provided via the input/output control interface 38 to the arithmetic unit 37 at suitable time intervals, starting the arithmetic operation for obtaining the membrane potential and the permeability coefficient of the vesicles to the lipophilic ions. After making sure that the values of the permeability coefficient and the membrane potential are respectively being converged to certain values, the arithmetic unit 37 causes the data input/output device 39 to record either one or both of the membrane potential and the permeability coefficient of the vesicular membrane to the lipophilic ions and then stops the arithmetic operation to be ready for the next measurement. The time for one measurement is about 10 minutes.

From the viewpoint of shortening the time for measurement, it is preferred to prepare a plurality of sets of the electrodes 13 and 14, the liquid 12 and the vessel 11 so that the outputs from these electrodes can alternately measured by the employment of a changeover switch.

That is, if during measurement with the electrode pair the other electrode pairs are all immersed in the liquid 12, the subsequent measurement can be started, immediately after the previous measurement, with the electrode pair whose output has become constant, thereby to ensure saving of the measuring time.

As described above, it is possible with this invention to directly and rapidly measure the basic factor defining the transport capacity of the vesicular membrane.

Next, this invention will be described more concretely in connection with its examples to show its effect and that the prescience of pathogens is possible with the membrane characteristics obtained with the method and the apparatus of this invention.

EXAMPLE 1

Figure 4:
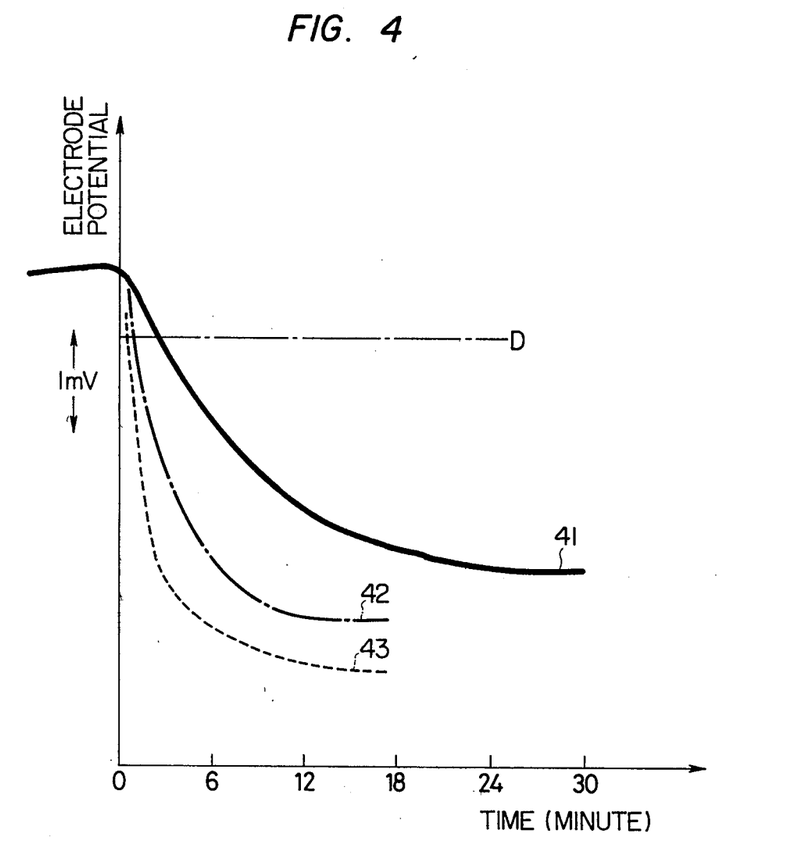
FIG. 4 is a graph showing electrode potential changes measured by the method and the apparatus of this invention in connection with erythrocytes of various animals.

Benzylphenyldimethylammonium (hereinafter referred to as BPDMA+) was selected as the lipophilic ion; tetraphenylboron anion (Tetraphenyl borate) was selected as an ion exchanger; their ion association is sealed in a plasticized vinyl chloride film 0.2 mm thick to produce the film 17 selectively responsive to BPDMA+; such a measuring system as shown in FIG. 1 was set up; and the constant-temperature bath 23 was held at 37° C. As the liquid for suspending vesicles, 2 ml of an aqueous solution of 153 mM, NaCl, 17 mM tris(hydroxymethyl)-aminomethane (hereinafter referred to as NaCl-Tris), whose pH was adjusted by hydrochloric acid to 7.4, was put in a silicone-treated glass vessel 11. After BPDMA+ was dissolved in NaCl-Tris in the vessel 11 so that the former became $10^{-5}$ M, the solution was left until the electrode potential became constant. Then, erythrocytes collected by the regular method from ox, man and rat were each injected to the abovesaid solution so as to account for 6% in hematocrit value. The resulting electrode potential changes are shown in FIG. 4, the abscissa representing time, the ordinate representing the electrode potential and curves 41, 42 and 43 indicating measured values for the ox, man and rat, respectively.

The value that the speed of the electrode potential change immediately after the injection of the erythrocyte is divided by the potential change until the electrode potential becomes constant again, is an index of the permeability of the red blood cell membrane for BPDMA+. The index of ox is the smallest, the index of man is larger than that of ox and the index of rat is the largest. According to a literature (L. L. M. Van Deenen & J. De Gier, Lipids of the Red Cell Membrane, In "The Red Blood Cell", edited by D. M. Surgenor, 2nd Ed., Academic Press, p. 147-p. 211, 1975), the abovesaid order agrees with the order of increase in the degree of unsaturation of fatty acid in the membrane of the red blood cell of these animals which is an index of the fluidity of the red blood cell membrane, and the order of increase in the permeability of the red blood cell membrane for phosphoric acid or glycerol, measured by another method. The results shown in FIG. 4 coincide with the general opinion that as the fluidity of biomembrane increases, its permeability also increases.

EXAMPLE 2

Tetraphenylphosphonium (hereinafter referred to as TPP+) was selected as the lipophilic ion and a film selectively responsive to TPP+ was produced by the same method as used in Example 1. The measuring system shown in FIG. 1 was set up and the temperature of the constant-temperature bath 23 was maintained at 16° C. As the liquid for suspending vesicles, 1 ml of an ordinary Ringer's solution was put in a silicone-treated glass vessel and TPP+ was dissolved in the solution so that the former became $10^{-5}$M, and then the solution was left until the electrode potential became constant. On the other hand, about $3 \times 10^7$ lymphocytes were collected from 5 ml of fresh blood of man, for example, by such an ordinary Angio-Conray-Ficoll method as set forth in a literature, Tissue typing using a routine one-step lymphocyte separation technique, Brit. J. Haematol. 18 (1970), 229–235, Harris, R. Ukaejiofo, E. O. The lymphocytes thus obtained were suspended in 1 ml of each of an RPMI 1640 solution containing 0.15 mg of phytohemagglutinin P (hereinafter referred to as PHA-P), which is one kind of lectin and a 1640 solution containing no PHA-P, and the suspensions, after being permitted to stand at 37° C. for 5 minutes, were centrifuged at 37° C. under 100 G for 10 minutes and then supernatants were removed to obtain lymphocyte samples (hereinafter referred to as sample E and F, respectively). When the samples E and F were each injected into the glass vessel 11 where the electrode potential became constant, the electrode potential momentarily decreased by the dilution effect but, thereafter, started to gradually drop, and in the period from 2 to 5 minutes after the injection, the electrode potential dropped at substantially a constant speed. The potential decreasing speed in the case of the sample E was higher than that in the case of the sample F by about 15%.

It is assumed that these phenomena are caused by the fact that when the lymphocytes are stimulated by PHA-P, the cell membrane possesses fluidity to facilitate flowing of the lipophilic ions into the lymphocytes. The phenomenon that the lymphocytes normally at rest are caused by an antigen stimulation, such as lectins, to transform to blast cells for proliferation and differentiation, is called lymphocyte blast formation phenomenon. By measuring the ratio of blastformed cells to all lymphocytes stimulated by antigens, it is possible to diagnose the degree of recovery of the immunological surveillance of patients, diagnose autoimmune diseases, identify the cause of allergy by drugs and detect the adaptability to organ transplantation. Such measurement of the ratio of blastformed cells to all lymphocytes stimulated by antigens already plays an important role in clinical examination and, further, the possibility of applying this measurement to early diagnosis and detection of relapse of cancer has also recently been reported; therefore, it is expected that this measurement will become more and more important.

A method that has heretofore been employed for measuring the abovesaid ratio is to fix the lymphocytes by dyeing, observe them under a microscope and count the number of lymphocytes transformed to blastcells, or to observe incorporation of 3H-thymidine into deoxyribonucleic acid (hereinafter referred to as DNA). However, these methods require a lot of time for the detection, involve complicated operations, such as sterile culture, and are difficult of automation, and hance are not suitable for processing of a large number of samples which are expected in future.

On the other hand, the phenomena described in respect of the present example indicate that the method and the apparatus of this invention enable early detection of the phenomenon of transformation of lymphocytes to blast cells and can be carried into practice as a method and an apparatus for rapid measurement of the ratio of blastformed cells to all lymphocytes stimulated by antigens.

EXAMPLE 3

TPP+ was selected as the lipophilic ions, the measuring system of FIG. 1 was set up by the same method as used in Example 2 and the temperature of the constant-temperature bath 23 was retained at 37°. As the liquid for suspending cells, 2 ml of NaCl-Tris was put in the silicone-treated glass vessel 11 and TPP+ was dissolved in the liquid so that the former became $10^{-5}$ M, and the solution was allowed to stand until the electrode potential became constant.

On the other hand, smooth muscle cells were extracted by the regular method from the cerebrovascular walls of a stroke-prone spontaneously hypertensive rat (hereinafter referred to as SHR-SP) aged 90 days and a normal tensive rat (Wistar-Kyoto) (hereinafter referred to WK) of the same day-age. The extracted smooth muscle cells were each injected into the glass vessel 11 so that the cells accounted for 5% in volume percentage. The changing rate of the electrode potential immediately after the injection of the smooth muscle cells of SHR-SP was higher than in the case of WK by about 10%. According to a literature (Jones, A. W. (1973) Circul Res. 35, 563–572), it is reported that the smooth muscle cells of SHR-SP is higher in the ion permeability of the cell membrane than in the case of WK. This shows that the permeability of the smooth muscle cell membrane can be measured by the method set forth in the present example.

EXAMPLE 4

In this example, the apparatus of FIG. 2 was utilized and, as the vesicles, red blood cells of man were used. As a sample containing the vesicles, blood (volume $V_S$=79 ul, hematocrit value Ht=38.0%, red blood cell density Nc=$3.89 \times 10^6$ cells/μl Blood) extracted from a peripheral vein of man was employed.

As the liquid for suspending the vesicles, NaCl-Tris was used and its volume $V_b$ was selected to be 1.5 ml.

As the lipophilic ions, TPP+ was used, whose concentration in the liquid 12 was selected to be $10^{-5}$ M.

The electrode 13 responsive to the lipophilic ions TPP+ was produced in the following manner: An ion association of TPP+ and tetraphenylboron anion (hereinafter referred to as TPB−) was produced by the regular method. In a solution in which polyvinyl chloride as a polymer, dioctyl phthalate as a plasticizer and dimethylformamide as a solvent were mixed in a ratio of 1 to 4 to 10 by weight, the abovesaid ion association was dissolved to account for 0.1% in weight percentage and a film 0.2 mm thick was made by the casting method. One portion cut out of the film was stuck by tetrahydrofuran to the top end portion of the plasticized vinyl chloride tube 16 having an inner diameter of 4 mm, an outer diameter of 6 mm and a length of 20 mm. TPP+ aqueous solution of $10^{-2}$ M was filled as the reference liquid 18 in the tube 16 and the tube was mounted on the top of a silver-silver chloride electrode HS-907 (Toa Electronics Ltd.) and used as the lipophilic ion electrode 13 selectively responsive to TPP+. As the reference electrode, HS-907 mentioned above was used.

As the vessel 11, a silicone-treated glass tube 15 mm in inner diameter and 40 mm in height was used and formed to receive the top end portions of the lipophilic ion electrode 13 and the reference electrode 14.

The other devices used are as follows: The speed control type electromagnetic stirrer 22 was a self-made one using a Q-con motor by Japan Servo Co., Ltd; the rotor 21 was an ordinary rotor 10 mm long; the constant-temperature bath 23 was a self-made one of acryl resin and having a hollow for housing the vessel 11; the constant-temperature warm water circulation pump 24 was a pump by Haake Inc. of West Germany; the injector 15 was a 100 μl micro syringe; the shield box 25 was a self-made one of aluminum; the impedance converter 31 was TR-8651 by Takeda Riken Co., Ltd.; the small DC voltage generator 32 was 3109 by Yokogawa Electric Works; the recorder 34 and the DC amplifier 35 were those by Yokogawa Electric Works; the A-D converter 36 was a converter of 8-bit resolution by Burrbrown Inc.; the input/output control interface 38 was an interface by Motorola Semiconductor Products Inc.; the data input/output device 39 was a combination of a keyboard input device and a thermal printer; and the arithmetic unit 37 was a combination of a memory circuit of 32K-byte capacity and a microprocessor. The program described in respect of FIG. 3 was used.

The temperature of the constant-temperature bath 23 was set to 37.0° C. As the potential difference between the lipophilic ion electrode 13 and the reference electrode 14 was −184 mV, a voltage of +184 mV was generated by the DC small voltage generator 32.

By connecting to the output side of the DC amplifier 35 a low-pass filter comprising a resistor of 10 KΩ and a tantalum capacitor of 10 μF, noise could be suppressed less than 10 μV. About an hour after turning on the power source switch for the entire apparatus, drift of the output from the DC amplifier 35 became about +0.1 mV/hr, so that data was entered in the arithmetic unit 37.

The data thus entered were the volume $V_b$(=1.5 ml) of the liquid 12 for suspending vesicles, the volume $V_s$ (=79 μl) of the injected blood, the hematocrit value Ht (=38.0%) of the injected blood, the erythrocyte density $N_c$(=3.89 $10^{-6}$ cells/μl Blood), the temperature T(=310.0° K) of the constant-temperature bath 23 and the cancelled voltage SUBPOT (=−184 mV) generated by the small voltage generator 32.

The volume $V^I$ of only the liquid 12 for suspending the erythrocytes and the total volume $V^{II}$ and the total surface area A of the injected erythrocytes, necessary for calculating P and $\Psi_m$ according to the equations (1) and (2) were calculated by the arithmetic unit 37 according to the following equations:

$$V^I = V_b + V_s(1 - \frac{Ht}{100})$$

$$V^{II} = V_s \cdot \frac{Ht}{100}$$

$$A = (160 \times 10^{-8}) \cdot (\frac{1}{90} \frac{\frac{Ht}{100} \times 10^{-9}}{N_c})^{\frac{2}{3}} \cdot (V_s \cdot N_C \cdot 10^3)$$

The equation for calculating A was set up on the assumption that the volume and the surface area of one standard erythrocyte of man were 90 μm$^3$ and 160 μm$^2$, respectively and that the erythrocytes, though different in size, are similar in shape.

The other parameters necessary for the calculation were all stored in the arithmetic unit 37. The values of the principal parameters are as follows: the time interval $\Delta t_1$ between the injection of the sample and the start of entering the output from the A-D converter 36 to the arithmetic unit 37 is 15 sec.; the time interval $\Delta t_2$ for entering the subsequent output from the A-D converter 36 to the arithmetic unit 37 is 6.0 sec.; the arithmetic operation starting moment $t_0$ is 51 sec.; the number of moments k shifting on the time base before and after the current moment when the shifting average value of the differential coefficient is obtained is 6; and the parameter $\epsilon_1$ necessary for stopping the calculation is equal to $\epsilon_2 = 0.01$.

When the blood of man was injected into the vessel 11 after completion of entering the above data, the arithmetic unit 37 began entering thereinto the output from the A-D converter 36 from the designated moment and conducted the calculation at each moment and typed out the calculation results.

Figure 5:
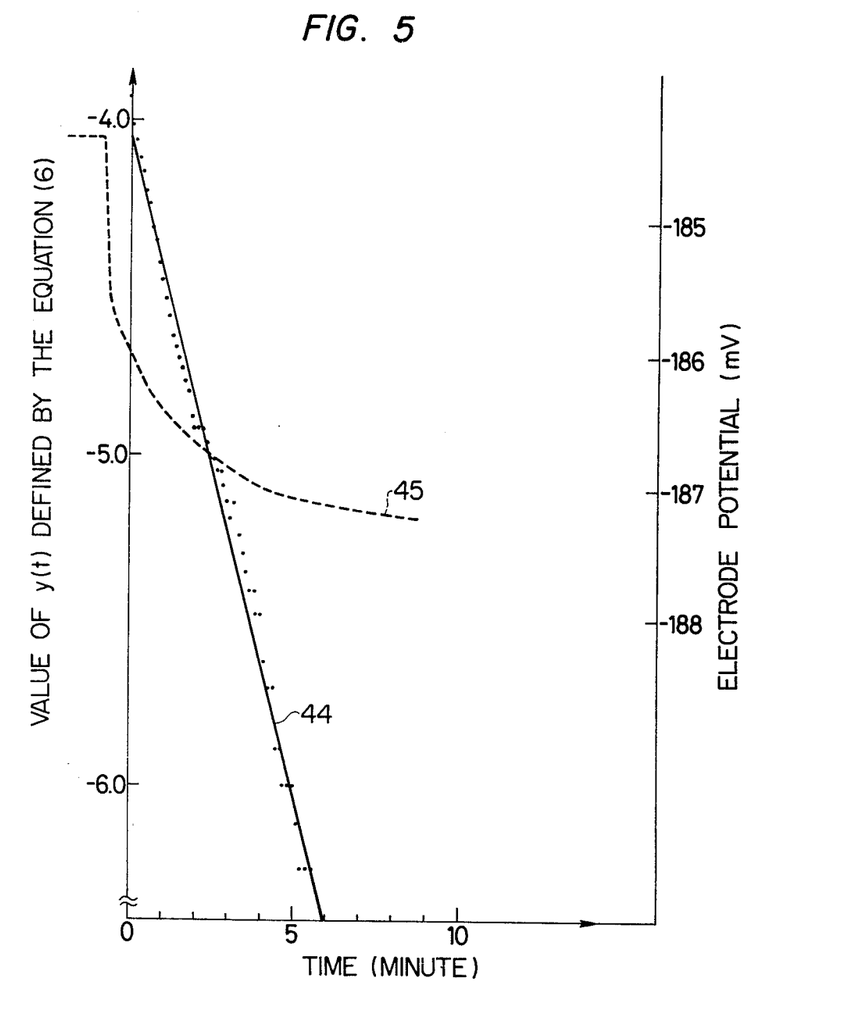
FIG. 5 is a graph showing values of the equation (7) described later and electrode potential changes when the membrane potential and the permeability coefficient for lipophilic ions (tetraphenylphosphonium) of a human erythrocytic membrane were measured by the method and the apparatus of this invention.

FIG. 5 shows curves by plotting the calculation results. The black dots are those by plotting against the moments DATAX(i) the value DATAY(i) of y(t) of the moment DATAX(i) defined by the equation (6) after starting the calculation; the solid line 44 is a straight line $y(t) = \hat{a} + \hat{b}(t - t_0)$ (At this time, $\hat{a} = -4.02$ and $\hat{b} = -0.399$); and the broken line 45 shows electrode potential variations recorded by the recorder 34. The calculation was stopped seven minutes after the start of calculation and the final calculation results in this case are as follows: the membrane potential $\Psi_m$ of the erythrocyte of man is $-30.8$ mV, the permeability coefficient P of the erythrocyte of man for TPP+ is $7.19 \times 10^{-7}$ cm/sec., and the coefficient of correlation RYYHAT between y(t) and $\hat{y}(t) = \hat{a} + \hat{b}t$ is 0.993. As is evident from FIG. 5 and the value of RYYHAT, y(t) of the equation (6) plotted for $t - t_0$ are almost on the straight line, warranting the measuring method of this invention. Further, the membrane potential and the permeability coefficient of the erythrocyte of man to TPP+ by the radio isotope method labelling TPP+ with tritium well coincided with the abovementioned values.

With the conventional membrane measuring methods, the operation cannot be conducted before the electrode potential becomes constant again after the injection of blood and this period may be relatively short because the speed of permeation of the lipophilic ion through the red cell membrane is large at such a high temperature as 37° C.; but more than 15 minutes is required. On top of that, it is necessary to follow the troublesome procedure of conducting a calculation by substituting the electrode potential variation into a complicated equation and only the membrane potential is obtained. On the other hand, the method of this invention produces a striking effect that the values of not only the membrane potential but also the permeability coefficient can simultaneously be obtained in a short time of about 7 minutes. Accordingly, this invention make a great contribution to medical researches and speeding up of clinical examination.

EXAMPLE 5

Figure 6:
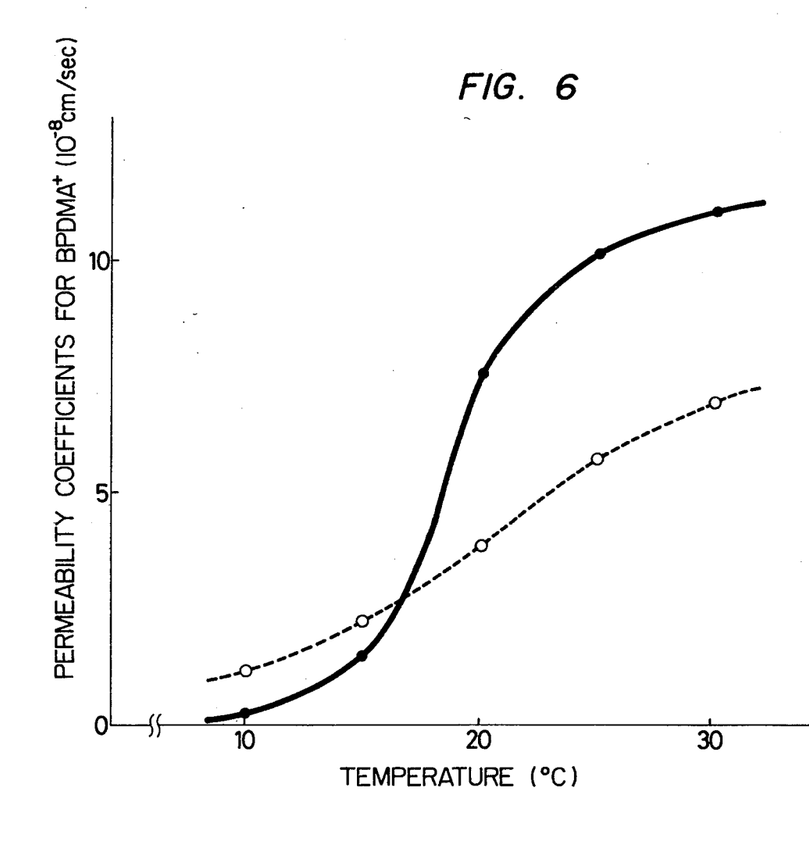
FIG. 6 is a graph showing the results of measurement of the permeability coefficient of liposome for lipophilic ions (benzylphenyldimethylammonium) obtained by the method and the apparatus of this invention under various temperature conditions.

This example was carried out under the same conditions as those of Example 4 except in using liposome as the vesicle and BPDMA+ as the lipophilic ion. Two kinds of liposome was prepared by the regular method; one containing only dimiristoylphosphatidyl choline (hereinafter referred to as the lipsome A) and the other containing dimiristoylphosphatidyl choline and cholesterol (hereinafter referred to as the liposome B). As the liquid in the liposome, use was made of sodium citrate solution of 154 mM, with pH adjusted to 7.4. The molar ratio of cholesterol in lipid of the liposome B was 37.5%. The permeability coefficients of the liposomes A and B for BPDMA+ were measured under various temperature conditions in the same manner as in the Example 4. The measured results, plotted against the temperature change, are shown in FIG. 6. Black circles are measured values for the liposome A and white circles are those for the liposome B. FIG. 6 shows that the liposomes used in this example also have the dual effect of cholesterol, i.e. the effect that the addition of cholesterol decreases the fluidity of a phospholipid membrane at temperatures above the phase transition point (in the vicinity of 20° C. in this example) of phospholipid and increases the fluidity at temperatures below the phase transition point. Thus, the use of the apparatus of this invention permits easy measurement of the temperature dependency of the permeability coefficient of the vesicular membrane to the lipophilic ion (corresponding to the fluidity of the vesicular membrane), by which it is possible to easily obtain valuable information in fundamental medicine and clinical medicine, such as the phase transition point of the vesicular membrane and so on. This is a great contribution to the progress of medicine.

EXAMPLE 6

Figure 7:
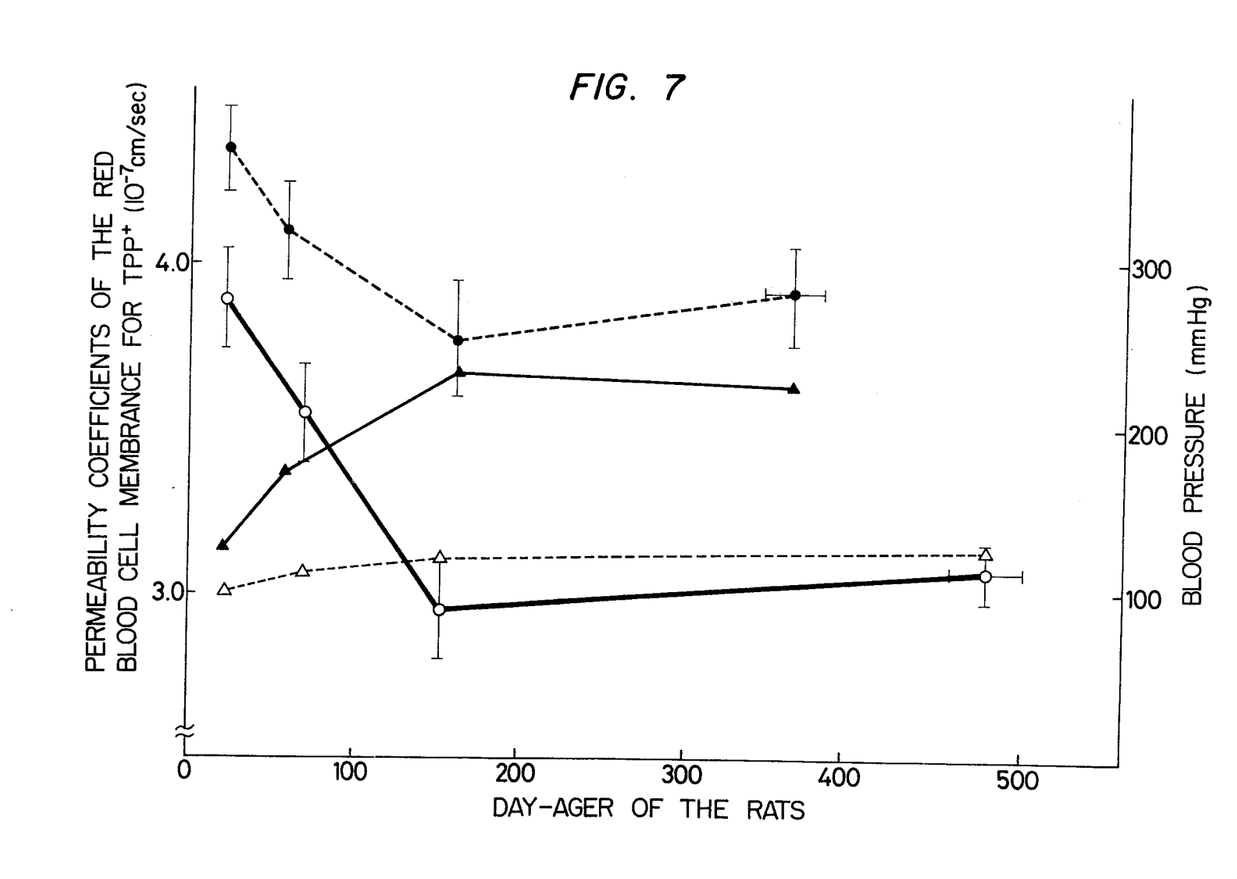
FIG. 7 is a graph showing the results of measurement of the permeability coefficient of erythrocytes collected from various aged rats for lipophilic ions (tetraphenylphosphonium) obtained by the method and the apparatus of this invention and the blood pressures of the rats.

Measurements were taken, in the same manner as in the Example 4, for the permeability coefficients to the lipophilic ion (TPP+) in connection with erythrocytes collected by the regular method from stroke-prone spontaneously hypertentive rats of various day-ages (SHR-SP) and normal tentive rats (WK) of various day-ages. The measured results are shown in FIG. 7 together with blood pressure variations with aging. The measurements were carried out at 17.5° C. Black and white circles respectively indicate the measured values of the permeability coefficients of the red blood cell membranes of SHR-SP and WK for TPP+, plotted against the day-ages of the rats. Black and white triangles respectively indicate the measured blood pressure values of SHR-SP and WK, plotted against the day-ages of the rats. The permeability coefficient of the red blood cell membrane of SHR-SP to TPP+ is significantly larger than those of WK before the blood pressure rises. This indicates that the prescience of the gene of stroke can be achieved by the method and the apparatus of this invention before the blood pressure rises.

What is claimed is:

1. An apparatus for measuring membrane characteristics of vesicles and comprising: p1 vessel means for containing vesicles and a solution of lipophilic ion;

electrode means, selectively responsive only to the lipophilic ion, for producing an output indicative of lipophilic ion concentration;

arithmetic unit means, electrically connected with said electrode means, for calculating the time-change rate of the detected output from said electrode means and also for calculating the permeability coefficient of the vesicular membrane for the lipophilic ion and/or the membrane potential of the vesicular membrane from said output of said electrode means, from said time-change rate, and from the following input data: the volume and temperature of the solution, and the total volume and the total surface area of the vesicles suspended in the solution; and input means for inputting said input data to said arithmetic unit means.

2. The apparatus according to claim 1 wherein said arithmetic unit means is digital arithmetic unit means.

3. The apparatus according to claim 1, wherein there is provided injector means for injecting a constant volume of the vesicles or lipophilic ion solution into the vessel.

4. The apparatus according to claim 3, wherein there is provided trigger signal generator means for applying to the arithmetic unit means an electric signal synchronized with the injecting operation of the injector means.

5. The apparatus according to claim 1, wherein there is provided a constant-temperature bath for holding the vessel means at a constant temperature.

6. The apparatus according to claim 1, wherein the vessel means and the electrode means are disposed in a shield box for cutting off electromagnetic noises.

7. The apparatus according to claim 1, wherein there is provided a recorder supplied with the detected output in analog form for recording it.

* * * * *